United States Patent [19]

Sanderson

[11] 4,342,324

[45] Aug. 3, 1982

[54] DENTAL FLOSSING FINGER

[76] Inventor: Paul E. Sanderson, 12 Rue Grand Vallee, Newport Beach, Calif. 92660

[21] Appl. No.: 234,483

[22] Filed: Feb. 17, 1981

Related U.S. Application Data

[63] Continuation of Ser. No. 13,744, Feb. 21, 1979, abandoned.

[51] Int. Cl.³ .............................................. A61C 15/00
[52] U.S. Cl. ................................................. 132/92 R
[58] Field of Search ..................................... 132/91–92

[56] References Cited

U.S. PATENT DOCUMENTS

| 1,389,064 | 8/1921 | Martin | 132/92 R |
| 1,468,942 | 9/1923 | Gamble | 132/92 R |
| 1,608,212 | 11/1926 | Hochstadter | 132/92 R |

Primary Examiner—G. E. McNeill
Attorney, Agent, or Firm—Knobbe, Martens, Olson, Hubbard & Bear

[57] ABSTRACT

A dental flossing holder and applicator is disclosed which is held in the user's hand and anchors one end of the floss, the free end of the floss being held and manipulated by the user's other hand.

3 Claims, 5 Drawing Figures

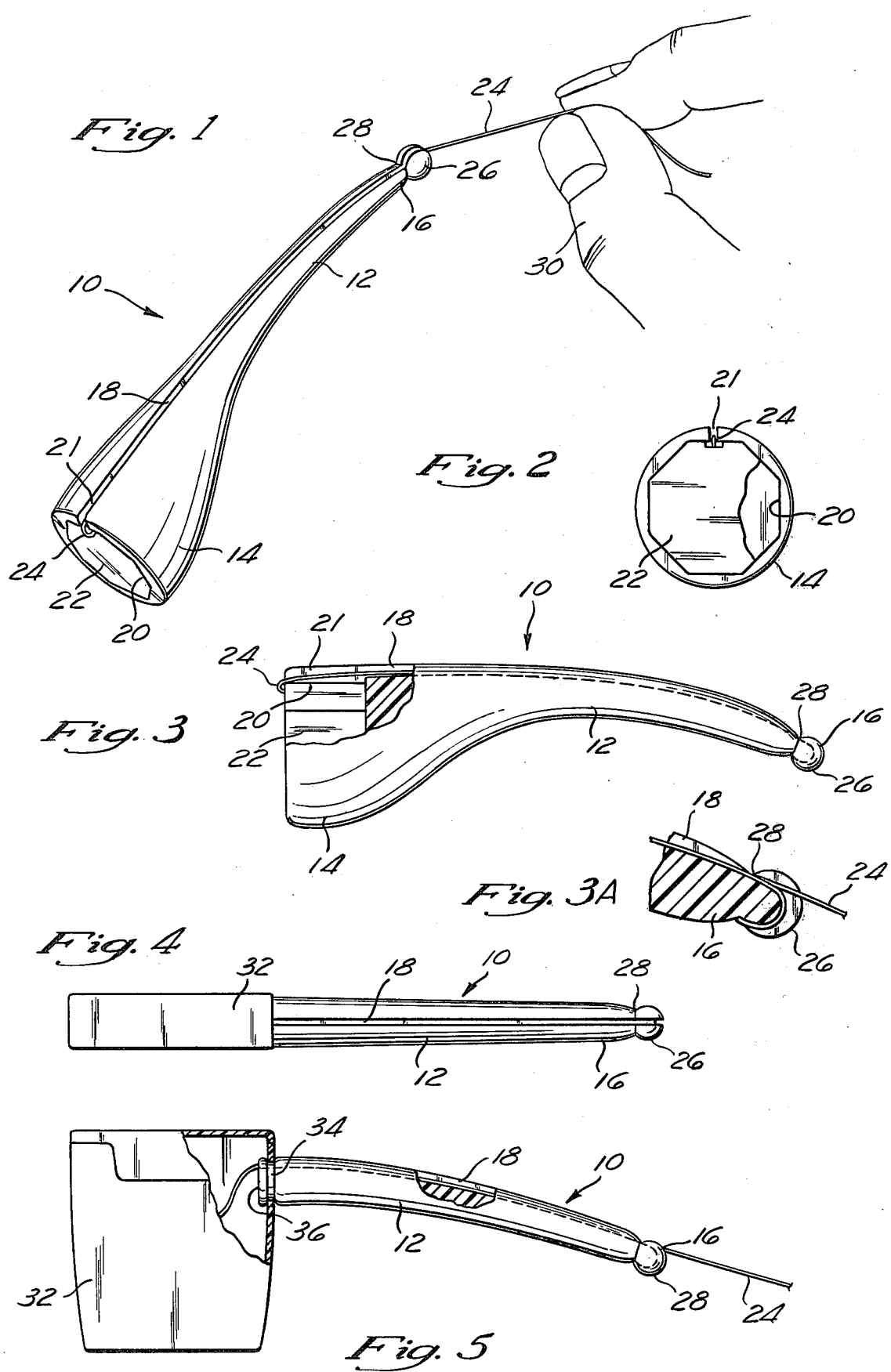

DENTAL FLOSSING FINGER

This application is a continuation of Ser. No. 13,744 filed 2/21/79 now abandoned.

BACKGROUND OF THE INVENTION

It is well known that flossing of the teeth is an important part of good dental hygiene. Many dentists recommend dental flossing to remove food particles that cannot be reached by the ordinary toothbrush. Dental floss is readily available in most pharmacies and drugstores in spool and cartridge dispensers.

Typically, flossing is accomplished by cutting a section of floss from the floss dispenser, pulling the floss from each end with the user's hands to create a tension in that section and then proceeding to floss the teeth. This, however, was not a very sanitary method nor did it provide easy manipulation of the floss during the flossing operation.

Various types of floss applicators and holders have been developed in an attempt to improve on the two-hand system. One such type of applicator is shown in U.S. Pat. No. 2,172,591, which illustrates a holder that can store the floss and also possesses a fork or prong by which one end of the floss is anchored, the other end being anchored at the spool. This applicator can be manipulated with only one hand of the user, however, it is difficult to reach the most rearward teeth and to regulate the tension in the floss. In addition, the user loses a sensation of the position of the floss and whether the floss is properly cleaning the teeth.

Another style of applicator is illustrated in U.S. Pat. No. 3,799,177. This patent shows a two-part tool which is manipulated with each hand of the user. Such two-member applicators suffer the disadvantages of being relatively cumbersome and difficult to manipulate and, again, do not give the user a sense of the position of the floss or whether the floss is functioning correctly.

A third style of applicator is a one-member system which is held in one of the user's hands and serves to anchor one end of the floss. The other end of the floss is then pulled with the user's other hand to create a tension. This type of applicator is shown in U.S. Pat. No. 3,393,687 and U.S. Pat. No. 3,831,611. This style of applicator is superior to the two-member or pronged applicators in that one of the user's hands grasps the free end of the floss and provides the user with the necessary sensitivity and ease of manipulation. This method, therefore, possesses an ease of manipulation unobtainable with the traditional two-hand method without losing a sense of the floss position for the user. These applicators, which may possess a storage means for the floss, suffer the disadvantages of requiring complicated winding and unwinding procedures for anchoring the floss and providing greater lengths of floss. These winding procedures make it difficult to ready the floss for use, to provide a new section of floss when the old is spent and to maintain the floss in a sanitary condition.

SUMMARY OF THE INVENTION

The disclosed invention is a novel dental floss holder which obviates the problems inherent in prior applicators. The invention possesses an elongate member having proximal and distal ends. The member is made of light-weight material such as molded plastic, is compact and is advantageously curved to facilitate easier manipulation of the applicator. The proximal end of the member contains means for retaining a cartridge of dental floss. The member possesses a longitudinal slot or channel, running its length for guiding and defining a path for said floss between said proximal and distal ends. The distal end has an anchoring means for anchoring the attached end of the floss, thereby leaving a free end of the floss which is then grasped with the other hand of the user to create a tension in the section of floss from the free end to the point of floss held at the anchoring means.

This convenient light-weight floss applicator and holder is extremely easy to use and serves as an extension of the user's finger. The disclosed invention, therefore, possesses all of the following advantages:

1. It is adapted for use with different commercially available spools and cartridges;
2. It is easily and inexpensively manufactured;
3. The floss can be anchored with no threading of any kind required;
4. It is easy to draw the floss from the storage spool by means of the longitudinal slot which requires no winding about the body of the member;
5. It is extremely simple to acquire more length of floss and to obtain a new section of floss for use by simply detaching the floss from the anchoring means and pulling the floss through the slot;
6. The tension in the section of floss used to clean the teeth can be easily regulated; and
7. The applicator provides a very sanitary method of flossing which requires minimum handling of the floss itself and since it does not require a winding of the floss about the member, provides minimum exposure of the floss environment. Thus, the floss applicator may be conveniently set upright upon its proximal end on sinks, washstands, and the like without soiling the floss.

BRIEF DESCRIPTION OF THE DRAWINGS

The features of the invention may be understood with reference to the following detailed description of illustrative embodiments of the invention, taken together with the accompanying drawings in which:

FIG. 1 is a perspective view of the preferred embodiment of the device.

FIG. 2 is an end view of the proximal end of the preferred embodiment of the device.

FIG. 3 is a plan, partially cut away view of a preferred embodiment of the device.

FIG. 3A is an enlarged plan sectional view of the distal end of a preferred embodiment of the device.

FIG. 4 is a top view of an alternative embodiment of the device.

FIG. 5 is a plan partially cut away view of an alternative embodiment of the device shown in FIG. 4.

DETAILED DESCRIPTION OF THE ALTERNATIVE EMBODIMENTS

FIG. 1 shows an embodiment of the dental floss holder and applicator 10 having an elongate member 12, a proximal end 14, a distal end 16 and an elongate slot or channel 18 extending the length of the member.

In the preferred embodiment, the device 10 is approximately four inches long and the member 12 is of a generally cylindrical shape. In this embodiment the member 12 is approximately one inch in diameter at the large or proximal end 14 and tapers down to approximately one-quarter inch at the distal end 16. The width of the slot 18 is slightly greater than the width of the floss. The depth of the slot is approximately 1/16 of an inch.

The member may be made of any light-weight durable, non-porous plastic such as that commonly used for manufacturing toothbrush handles. The member could be molded from this plastic material such as by injection molding as is well known to those of ordinary skill in the art. This material and method allows the invention to be manufactured economically and easily.

Preferably, the device will have means for retaining a cartridge of floss. Commercially available floss cartridges come in various sizes and shapes and generally have an exterior housing which contains a spool of floss. FIG. 2 depicts a preferred embodiment of the device which has a retaining means suitable for retaining floss cartridges of a size somewhat smaller than the proximal end 14 of the device. Referring to FIG. 2, the proximal end 14 possesses a hollow recess 20 which extends into the proximal end for approximately one-half inch in a direction generally parallel to said longitudinal slot thereby forming a convenient cavity for retaining the cartridge 22. The enlarged proximal end also serves as a convenient base for setting the member upright on sinks and the like without soiling the floss when the unit is not being used. As shown in FIGS. 2 and 3, advantageously, the end portion 21 of the slot 18 extends through the wall of the proximal end 14 such that the slot 18 is in direct communication with recess 20 thereby forming a passageway so that the floss contained within the cartridge can be drawn from the recess 20 through 21 and positioned within the slot 18 running longitudinally along the member 12.

The hollow recess 20 is an example of a preferred retaining means, however, many other possible configurations can be made which will be suitable for retaining a floss cartridge as is apparent to those in the art. These various possible configurations for the retaining means allows the member to be readily adaptable for retaining many different commercially available cartridges.

As can be seen most clearly in FIG. 3, the applicator 10 in the preferred embodiment is of a curved configuration. The curve which inherently possesses convex and concave sides makes it easier to floss the teeth, in that the unit can be curved upward when one is flossing upper teeth and curved downward when flossing lower teeth.

Referring to FIGS. 1 and 2, after the floss cartridge 22 is placed within the recess 20, the free end of the floss 24 is pulled through the passageway thereby positioning the floss within the slot 18. Further pulling upon the free end of the floss 24 will draw floss through the path defined by the slot 18 along the member 12. The slot therefore serves to guide the floss through a path which it defines and further serves to shield the floss from the environment thereby keeping it in a more sanitary condition. The slot eliminates the need for complicated winding procedures in order to draw more floss from the cartridge. Advantageously, the slot 18 is along the convex side of the curve which facilitates dispensing of the floss from the cartridge.

At the distal end 16, there is an anchoring means 26 shown most clearly in FIG. 3A which preferably is an enlarged knob. The knob which is of a generally spherical shape possesses a narrow base 28. An extension of the slot 18 extends approximately three-quarters of the circumference of the knob 26 as shown in FIG. 3A.

In order to make the unit 10 ready for use, the user's hand 30 will grasp the free end of the floss 24, and pull it through the slot including that portion of the slot running along the knob which is on the convex side of the member. This should be done until a desired length of floss is achieved for flossing the teeth as measured from the knob 26 to the free end 24 grasped by the hand 30. The user then pulls the free end of the floss 24 with a force and angle such that the floss is positioned throughout the knob's slot including that portion on the concave side of the member. This will result with the free end of the floss extending from the base of the knob at the concave side of the member. The user then winds the floss about the base 28 of the knob 26 in order to anchor the floss, thereby preventing more floss from being drawn from the cartridge. The end of the floss which is attached to the cartridge 22 is anchored from the combination of the wrapping of the floss about the base 28 and the fact that the floss is threaded within the slot along the knob. This ease in anchoring the floss is a distinct advantage of the invention which requires no complicated winding procedures around a prong or around the applicator in order to anchor the floss.

As the user applies force to the free end of the floss 24 with hand 30, there is a tension created in the section of floss which runs from the point of anchoring 26 to the free end. This tension can readily be controlled by the user unlike the above described applicators which involve a fork or prong. Having completed these simple steps, the floss applicator is now ready for use.

If the user should desire a greater length of usable floss or if he should require a new section of floss, he need simply unwind the floss from the base 28, thereby again freeing the end of the floss which is attached to the cartridge. This then allows the user to draw more floss from the cartridge 22 in an easy efficient manner without complex unwinding procedures. Used sections of floss can easily be cut off by use of a cutter (not shown) typically included with the floss cartridge.

FIGS. 4 and 5 illustrate an alternative embodiment of the invention showing a larger square shaped floss cartridge 32 which is attached to the dental floss holder and applicator 10. In this embodiment, the proximal end 14 of the member 12 is only about one-half inch in diameter. An annular groove 34 which forms a plane generally perpendicular to said member is cut at a position about one-eighth of an inch distal to the proximal end. Said groove 34 thereby forms a rim 36 at the extreme proximal end of the member. An aperture is cut into the cartridge housing with a circumference approximately equal to the circumference of the annular groove. The proximal end 14 is then pushed through the aperture in the cartridge 12 up to the annular groove. The cartridge is thereby securely retained due to the relation of the larger diameter of the knob 26 with respect to the diameters of the aperture in the cartridge and of the annular groove 34 which prevents the member from being withdrawn from the cartridge. In this embodiment because of the larger size of the floss cartridge 32, the retaining means is not in the form of a hollow recess, but rather includes the rim 36 and annular groove 34 which act to conveniently retain the cartridge on the elongate member 12.

I claim as my invention:

1. A holder and applicator for dental floss comprising in combination:

a single unitary elongated applicator body member having (a) proximal and distal ends, (b) a generally circular cross section which smoothly diminishes in area between said proximal and distal ends, and (c) a streamlined exterior wall having a substantially continuously even surface forming a convex curve on one side of said body member and a concave curve on the opposite side of said body member, said proximal end forming an enlarged base for setting said holder and applicator upright when it is not being used so as to maintain the floss in a sanitary, unsoiled condition;

said body member having a generally cylindrical hollow recess formed in said proximal end for retaining a cartridge of dental floss;

anchoring means located at the distal end of said body member, said anchoring means comprising (a) an enlarged knob integral to said body member located at the extreme end of said body member and (b) a neck portion of smaller radius at the base of said knob around which the dental floss is easily wrapped for temporarily anchoring said floss at the distal end of said body member and leaving a loose end of floss hanging freely from said distal end for flossing teeth; and floss pathway means comprising:

(a) a longitudinal open slot in the convex curved side of the exterior surface of said body member and extending the length thereof, (b) a slot in the wall of the proximal end of said body member so that said hollow recess is in direct communication with said longitudinal slot, and (c) an open slot in said enlarged knob in communication with said longitudinal slot;

said floss pathway means formed providing a defined, protected and easily threaded pathway for floss from (a) said point of egress of the floss to the exterior wall of said body member to (b) said anchoring means so that the user of said holder and applicator need only withdraw a length of floss from said point of egress, lay said length of floss into said open longitudinal slot, lay said floss into said open slot in said enlarged knob, and anchor the floss around said neck portion of said anchoring means.

2. A holder and applicator for dental floss comprising in combination:

a unitary elongated applicator body member having (a) proximal and distal ends, (b) a generally circular cross section between said proximal and distal ends, and (c) a streamlined exterior wall having a substantially continuously even surface forming a convex curve on one side of said body member and a concave curve on the opposite side of said body member, said proximal end forming an enlarged base for setting said holder and applicator upright when it is not being used so as to maintain the floss in a sanitary, unsoiled condition;

means for retaining a cartridge of dental floss at the proximal end of said body member;

anchoring means located at the distal end of said body member, said anchoring means comprising (a) an enlarged knob integral to said body member located at the extreme end of said body member and (b) a neck portion of smaller radius at the base of said knob around which the dental floss is easily wrapped for temporarily anchoring said floss at the distal end of said body member and leaving a loose end of floss hanging freely from said distal end for flossing teeth; and floss pathway means comprising:

(a) a longitudinal open slot in the convex curved side of the exterior surface of said body member and extending the length thereof, and (b) an open slot in said enlarged knob in communication with said longitudinal slot;

said floss pathway means provides a defined, protected and easily threaded pathway for floss from said cartridge to said anchoring means so that the user of said holder and applicator need only withdraw a length of floss from said point of egress, lay said length of floss into said open longitudinal slot, lay said floss into said open slot in said enlarged knob, and anchor the floss around said neck portion of said anchoring means.

3. A holder and applicator for dental floss comprising:

an elongated applicator member having a streamlined wall and a substantially continuously even surface between its proximal and distal ends;

housing means located at the proximal end of said elongated member for retaining a cartridge of dental floss;

anchoring means located at the distal end of said applicator member for anchoring the floss at said distal end to leave a length of floss hanging freely for flossing teeth; and means for providing a convenient and easily threaded path for said floss extending from said housing means to said anchoring means, said means comprising a longitudinal slot in said elongated member, extending the length thereof between said cartride and said anchoring means, said slot being open to the atmosphere substantially along its length so that the user of said holder and applicator need simply place a cartridge of floss in said housing means, withdraw a length of floss from said housing means, lay said length of floss into said open slot, and anchor the floss at said anchoring means.

* * * * *